US008715733B2

(12) United States Patent
Kadiyala et al.

(10) Patent No.: US 8,715,733 B2
(45) Date of Patent: May 6, 2014

(54) ENHANCED ADIPOSE TISSUE

(75) Inventors: Sudhakar Kadiyala, Newton, MA (US); Mohamed Attawia, Holmdel, NJ (US); Thomas M DiMauro, Southboro, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 1509 days.

(21) Appl. No.: 11/189,336

(22) Filed: Jul. 26, 2005

(65) Prior Publication Data

US 2006/0018887 A1 Jan. 26, 2006

(51) Int. Cl.
*A61K 38/18* (2006.01)
(52) U.S. Cl.
USPC .......................... 424/488; 424/93.7; 424/484
(58) Field of Classification Search
None
See application file for complete search history.

(56) References Cited

U.S. PATENT DOCUMENTS

| | | | |
|---|---|---|---|
| 3,886,948 | A | 6/1975 | Hakim |
| 4,332,255 | A | 6/1982 | Hakim et al. |
| 4,387,715 | A | 6/1983 | Hakim et al. |
| 4,551,128 | A | 11/1985 | Hakim et al. |
| 4,595,390 | A | 6/1986 | Hakim et al. |
| 4,615,691 | A | 10/1986 | Hakim et al. |
| 4,772,257 | A | 9/1988 | Hakim et al. |
| 4,816,016 | A | 3/1989 | Schulte et al. |
| 5,176,627 | A | 1/1993 | Watson |
| 5,282,864 | A | 2/1994 | Noiles et al. |
| 5,928,182 | A | 7/1999 | Kraus et al. |
| 6,083,919 | A | 7/2000 | Johnson et al. |
| 6,352,557 | B1 | 3/2002 | Ferree |
| 6,419,944 | B2 | 7/2002 | Tobinick |
| 6,503,507 | B1 | 1/2003 | Allen |
| 6,527,759 | B1 | 3/2003 | Tachibana et al. |
| 6,592,888 | B1 | 7/2003 | Jensen et al. |
| 6,605,751 | B1 | 8/2003 | Gibbins et al. |
| 2002/0026244 | A1 | 2/2002 | Trieu |
| 2003/0039651 | A1 | 2/2003 | Olmarker |
| 2003/0049256 | A1 | 3/2003 | Tobinick |
| 2003/0125679 | A1 | 7/2003 | Kubota et al. |
| 2003/0161816 | A1 | 8/2003 | Fraser |
| 2003/0204229 | A1 | 10/2003 | Stokes |
| 2004/0193274 | A1 | 9/2004 | Trieu |
| 2005/0048644 | A1 | 3/2005 | Hedrick et al. |

FOREIGN PATENT DOCUMENTS

| | | |
|---|---|---|
| EP | 0990924 | 4/2000 |
| WO | WO 02/100387 A1 | 12/2002 |
| WO | WO 2005/049055 A | 6/2005 |

OTHER PUBLICATIONS

Alini, Eur. Spine J., *A Biological Approach to Treating Disc Degeneration: Not for Today, but Maybe for Tomorrow*, 11 (Supp. 2), 2002, pp. S215-S220.
Ardehali, J. Biomed., *The Inhibitory Activity of Serum to Prevent Bacterial Adhesion is Mainly Due to Apo-transferrin*, Mat, Res., Jul. 1, 2003, 66, 1, pp. 21-28.
Cassatella, J. Exp. Med. *Interleukin 10 (IL-10) Inhibits the Release of Proinflammatory Cytokines. . .* , 1993, Dec. 1, 178(6), pp. 2207-2211.
Cassatella, J. Exp. Med., *Interleukin 10 (IL-10) Upregulates IL-1 Receptor Antagonist Production . . .* ,1994, May 1, 179(5) pp. 1695-1699.
Desai, Anal. Biochem., *Coated Microwefi Plate-based Affinity Purification of Antigens*, May 15, 2004, 328(2), pp. 162-165.
Diez, Eur. J. Endocrinology, *The Role of the Novel Adipocyte-derived Hormone Adiponectin in Human Disease*, 2003, 148, pp. 293-300.
Goupille, Spine, *Matrix Metalloproteinases: The Clue to Intervertebral Disc Degeneration?*, 23(14), 1998, pp. 1612-1626.
Guillen, Arthritis, Rheum., *The Effects of Local Administration of Lactoferrin on Inflammation in Murine Autoimmune and Infectious Arthritis*, 43, 2000, pp. 2073-2780.
Hayashida, Eur. J. Pharmacology, *Lactoferrin Enhances Peripheral Opioid-mediated Antinociception via Nitric Oxide in Rats*, 484, 2004, pp. 175-181.
Hayashida, J. Vet. Med. Sci., *Oral Administration of Lactoferrin Inhibits Inflammation and Nociception in Rat Adjuvant-Induced Arthritis*, 66(2), 2004, pp. 149-154.
Karppinen, Spine, *Tumor Necrosis Factor-α Monoclonal Antibody, Infliximab, Used to Manage Severe Sciatia*, 28(8), 203, pp. 750-754.
Kumada, Circulation, *Adiponectin Specifically Increased Tissue Inhibitor of Metalloproteinase-1 Through Interleukin-10 . . .* , May 4, 2004, 109(17) pp. 2046-2049.
Matsuda, J. Biol. Chem., *Role of Adiponectin in Preventing Vascular Stenosis*, 277(40) pp. 37487-37491.
Motoshima, Biochem. Biophys. Res. Comm., *Adiponectin Suppresses Proliferation and Superoxide Generation and Enhances eNOS Activity. . .* , 2004, 315, pp. 264-172.
Nakano, J. Biochem (Tokyo), *Isolation and Characterization of GBP28, a Novel Gelatin-Binding Protein Purified from Human Plazma*, Oct. 1996, 120(4), pp. 803-812.
Ohko, J. Biomed. Mat. Res. (Appl Biomet), *Self-Sterilizing and Self-Cleaning of Silicone Catheters Coated with $TiO_2$Photocatalyst Thin Rims: A Preclinical Work*, 58, 2001, pp. 97-101.
Ouichi, Circulation, *Adipocyte-derived Plasma Protein, Adiponectin, Suppresses Lipid Accumulation and Class A Scavenger Receptor Expression*, . . . 103(8), Feb. 27, 2001, p. 1057.
Ouichi, Circulation, *Novel Modulator for Endothelial Adhesion Molecules . . .* ,1999, 100, pp. 2473-2476.
Brakenhielm, PNAS, *Adiponectin-induced Antiangiogenesis and Antitumor Activity Involve Caspase-Mediated Enhothelial Cell Apoptosis*, 101(8), pp. 2476-2481.
Shanbhag, J. Biomed. Mar. Res., *Decreased Neutrophil Respiratory Burst on Exposure to Cobalt-Chrome alloy and Polystyrene in vitro*, vol. 26, 1992, pp. 185-195.
Shimada, Clin., Chim. Actga. *Adiponectin and Atherosclerotic Disease*, Jun. 2004, 344(1-2), pp. 1-12.

(Continued)

*Primary Examiner* — Gregory S Emch

(57) ABSTRACT

An enhanced adipose tissue containing native adipose tissue and a concentrated amount of an active agent derived from adipose tissue, wherein the enhanced adipose tissue is preferably injected into the intervertebral disc of a patient suffering from degenerative disc disease.

7 Claims, No Drawings

(56) References Cited

OTHER PUBLICATIONS

Singh, Nature, *A Component of Innate Immunity Prevents Bacterial Biofilm Development*, 417, May 30, 2002, pp. 552-555.
Talukder, J. Vet. Med. Sci. *Receptor-Mediated Transport of Lactoferrin into the Cerebrospinal Fluid via Plasma in Young Calves.*, 65(9), 2003, pp. 957-964.
Taylor, Regul. Toxicol. Pharmacol. *Safety Determination for the use of Bovine Milk-derived Lactoferrin as a Component of an Antimicrobial Beef Carcass Spray*, Feb. 2004, 39(1), pp. 12-24.
Trampuz et al., *Clin. Orthop, Molecular and Antibiofilm Approaches to Prosthetic Joint Infection*, (414), 2003, pp. 69-88.
Trif, Exp. Biol. Med (Maywood), *Liposomes as Possible Carriers for Lactoferrin in the Local Treatment of Inflammataory Diseases*, 226(6), 2001, pp. 559-564.
Tobinick, Swiss Med.Weekly, *Perispinal TNF-alpha Inhibition for Discogenic Pain*, 2003, 133, pp. 170-177.
Wulster-Radcliffe, Biochem, Biophys. Res. Comm., *Adiponectin Differentially Regulates Cytokines in Porcine Macrophages*, 316, 2004, pp. 924-929.
Yamamoto, Biochem. Biophys. Res. Comm., *Effect of Interleukin-10 on the Gene Expression of Type I Collagen, Fibronectin, and Decorin in Human Skin Fibroblasts: Differential Regulations by Transforming Growth Factor-β and Monocyte Chemoattractant Protein-1*, 316, 2004, pp. 924-929.
Yokota, Blood, *Adiponectin, a New Member of the Family of Soluble Defense Collagens, Negatively Regulates the Growth of Myelomonocytic Progenitors and the Functions of Macrophages*, Sep. 1, 2000, 96(5), pp. 1723-1732.
Brennen, Rheumatology, *Interleukin 10 and Arthritis*, 38, 1999, pp. 293-297.
Carmody et al., Arthritis & Rheumatism, *Viral Interleukin-10 Gene Inhibition of Inflammation* . . . , 46(5), May 2002, pp. 1298-1308.
Goodman et al., JBMR, *Modulation of Bone Ingrowth and Tissue Differentiation by Local Infusion of Interleukin-10* . . . , 65A, 2003, pp. 43-50.
Hart et al., Immunology, *Comparison of the suppressive Effects of Interleukin-10 and Interieukin-4 on Synovial Fluid Macrophages and* . . . , 84(4), Apr. 1995, pp. 536-542.
Pollice et al., J. Orthop Res., *Interleukin-10 Inhibits Cytokine Synthesis in Monocytes Stimulated by Titanium Particles:* . . . , 16(6), Nov. 1998, pp. 697-704.
Trindade et al., Biomaterials, *Interleukin-10 Inhibits Polymethylmethacrylate Particle Induced Interleukin-6 and Tumor Necrosis* . . . , 22, 2001, pp. 2067-2073.
Hughes et al., Rheumatology, *Interleukin 10 and Arthritis*, 38, 1999, pp. 293-297.
Maeda, S. at al., Spine, *Changes with Age in Proteoglycan Synthesis in Cells Cultured in Vitro from the Inner and Outer Rabbit Annulus Fibrosus*, vol. 25(2), 2000, pp. 166-169.
Schierholz J M et al, "Development of a New CSF-Shunt with Sustained Release of an Antimicrobial Broad-Spectrum Combination", Zentralblatt fur Bakteriologie, Jun. 1997, pp. 107-123, vol. 286, No. 1.
Wang, Y. et al., "Adiponectin Inhibits Cell Proliferation by Interacting with Several Growth Factors in an Oligomerization-dependent Manner", The Journal of Biological Chemistry, vol. 280, No. 18, May, pp. 18341-18347.
Shibata, R. et al., "Adiponectin Stimulates Angiogenesis in Response to Tissue Ischemia through Stimulation of AMP-activated Protein Kinase Signaling", The Journal of Biological Chemistry, vol. 279, No. 27, July, pp. 28670-28674.
Eng, J. et al., *Effects of Pronounced Weight Loss on Adiponectin Oligomer Composition and Metabolic Parameters*, Obesity, May 5, 2007, vol. 15(5), pp. 1172-1178.
Man, K. et al., *Fat-Derived Hormone Adiponectin combined with FTY720 Significantly Improves Samm-for-Size Fatty Liver Graft Survival*, Am. J. Transplation, 2006, vol. 6, pp. 467-476.
Pajvani, "Structure-Function Studies of the Adipocyte-Secreted Hormone Acrp30/Adiponectin, The Journal of Biological Chemistry"; 2003; pp. 9073-9085; vol. 278(11); The American Society for Biochemistry & Molecular Biology, Inc.
Engi, "Effects of Pronounced Weight Loss on Adiponectin Oligomer Composition and Metabolic Parameters"; Obesity; May 5, 2007; pp. 1172-1178; Vo. 15(5); NAASO.
Tsao, "Role of Disulfide Bonds in Acrp30/Adiponectin Structure and Signaling Specificity"; The Journal of Biological Chemistry; Dec. 12, 2003; pp. 50810-50817; vol. 278(50); The American Society for Biochemistry and Molecular Biology, Inc.
Waki, "Impaired Multimerization of Human Adiponectin Mutants Associated with Diabetes"; The Journal of Biological Chemistry; Oct. 10, 2003; pp. 40352-40363; vol. 278(41); The American Society for Biochemistry and Molecular Biology, Inc.
Wang, "Proteomic and Functional Characterization of Endogenous Adiponectin Purified From Fetal Bovine Serum"; Proteomics; 2004, pp. 3933-3942; vol. 4; Wiley-VCH Verlag GmbH & Co. KGaA, Weinheim.

ENHANCED ADIPOSE TISSUE

CONTINUING DATA

This application claims the benefit of U.S. Provisional Patent Application Ser. No. 60/590,526, entitled "Intradiscal Anti-Inflammatory Therapy Involving Autologous Adiponectin", filed Jul. 23, 2004, and is a continuation-in-part claiming priority from U.S. patent application Ser. No. 10/938,905, entitled "Intradiscal Anti-Inflammatory Therapy Involving Autologous Adiponectin", filed Sep. 10, 2004, the specifications of which are incorporated by reference in their entireties.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1β and TNF-α as well as matrix metalloproteinases ("MMPs"). These cytokines and MMPs help regulate the metabolism of the nucleus pulposus cells.

In some instances of disc degeneration disease (DDD), gradual degeneration of the intervetebral disc is caused by mechanical instabilities in other portions of the spine. In these instances, increased loads and pressures on the nucleus pulposus cause the cells within the disc (or invading macrophases) to emit larger than normal amounts of the abovementioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix, in particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, causing the nucleus pulposus to contact the spinal cord and produce pain.

U.S. Published Patent Application No. 2005/0048644 (Hedrick) discloses methods of treating patients including the processing of adipose tissue to deliver a concentrated amount of regenerative cells (e.g., stem cells) obtained from the adipose tissue to the patient. Hedrick teaches that the regenerative cells may be used to promote the production of proteoglycan rich matrix in intervertebral disc repair, and so may be used to treat a degenerative disc disease. Finally, Hedrick discloses that the regenerative cells may be used in their 'native' form as present in or separated and concentrated from the tissue.

SUMMARY OF THE INVENTION

The present inventor has appreciated that adipose tissue not only has mechanical qualities that are desirable for its use in treating DDD, but also contains active agents (such as adiponectin) that are desirable for treating DDD as well. The present inventor has further recognized that these agents are amenable to concentration from their native levels in adipose tissue to provide a heightened therapeutic effect in the disc. Accordingly, the present inventor has developed an enhanced adipose tissue whereby an active agent from a first portion of adipose tissue is first concentrated (for example, by extraction) to a level above its native level normally present in adipose tissue and then added to native adipose tissue. The resulting product has mechanical properties substantially similar to native adipose tissue and will contain an active adipose-derived agent present in a concentration greater than that found in native adipose tissue.

Therefore, in accordance with the present invention, there is provided a graft derived from adipose tissue comprising a native level of an active agent, comprising:
  a) native adipose tissue, and
  b) an active agent derived from adipose tissue and present at a level greater than the native level of the active agent in adipose tissue.

Also in accordance with the present invention, there is provided a method of making a graft derived from adipose tissue, comprising:
  a) obtaining native adipose tissue,
  b) separating the adipose tissue into a first portion and a second portion,
  c) concentrating an active agent from the first portion, and
  d) combining the concentrated agent with the second portion to produce an enhanced adipose tissue, and
  e) introducing the enhanced adipose tissue into an intervertebral disc.

DETAILED DESCRIPTION

In some embodiments, the active agent is a protein. In preferred embodiments, the protein is selected from the group consisting of IRAP, IL-10 and adiponectin.

Adiponectin ("APN") may be selected as the active agent for its anti-inflammatory properties. The literature appears to recognize the anti-inflammatory nature of APN. Shimda reports that adiponectin has protective actions in the initiation and progression of atherosclerosis through anti-inflammatory and anti-atherosclerotic effects." Shimada, *Clin. Chim. Acta*, 2004, June 344(1-2):1-12. Yokota indicates that APN is involved in the termination of inflammatory responses, and suggests that APN may have therapeutic applications in diseases caused by excessive inflammatory responses." Yokota, *Blood*, 1 Sep. 2000 96(5), 1723-1731. Diez concludes that the ability of APN to increase insulin sensitivity in connection with its anti-inflammatory and anti-atherogenic properties have made this novel adipocytokine a promising therapeutic tool for the future". Diez, *Eur. J. Endocrinology* (2003) 148, 293-300.

APN antagonizes TNF-α. Yokota, *Blood,* 2000, Sep. 1, 96(5), 1723-32 reports that about 10 ug APN/I inhibits phagocytic activity and completely eliminates TNF-α production from LPS-induced phagocytes. In particular, Yokota reported that LPS-induced production of TNF-α in human macrophages dropped from over 800 pg/ml TNF-α to less than 20 pg/ml TNF-α when only 10 ug/l APN was applied. Yokota concluded that APN is an important negative regulator of immune systems, may be a unique suppressor of inflammatory responses because of its specific inhibition of TNF-α transcription, may be involved in ending inflammatory responses, and may have therapeutic applications in diseases casued by excessive inflammation.

Wulster-Radcliffe, *Biochem. Biophys. Res. Comm.,* 316 (2004), pp. 924-929, also reports that pretreatment of human macrophages with 10 µg/ml APN suppressed TNF-α production by about 50%, and hypothesized that some of the anti-inflammatory actions thereof are mediated in part by APN suppression of NFκB signaling and ERK1/2 activity.

If APN is selected then it may be concentrated separating adipose tissue into first and second portions, removing liquid containing adiponectin from the first portion, and then passing the liquid through an affinity column containing a separation material for which APN has a high affinity. The APN is thus preferentially adsorbed onto the separation material. Next, adsorbed APN is eluted from the separation material using a suitable elution solution. The eluted APN is then combined with the second portion of native adipose tissue.

In some embodiments, liquid from the first portion of adipose tissue can be obtained by simply compressing the tissue, and collecting the liquiud that exudes from the tissue during compression.

In some embodiments, the separation material is a gelatin. Nakano, *J. Biochem* (Tokyo), 1996 Oct. 120(4) 803-12, examined methods for isolating APN, and found not only that APN binds specifically to gelatin, but also that it can be eluted from the gelatin material by a 1M NaCl solution. Nakano further reported that applying these methods to 500 ml of human plasma resulted in the isolation of about 50 µg of APN.

Since APN is typically present in native serum at a concentration of about 1.9-17 µg/ml, it is desired that the final graft comprise an enhanced level of adiponectin of at least 10 µg/ml, more preferably at least 15 µg/ml, more preferably at least 20 µg/ml.

IRAP may be selected as the active agent for its anti-inflammatory properties. The literature appears to recognize the anti-inflammatory nature of IRAP.

Some investigators have proposed treating DDD by administering recombinant IRAP in order to that specifically antagonize pro-inflammatory cytokine IL-1B. For example, Maeda et al. *Spine* 25(2):166-169 (2000) reports on the in vitro response to recombinant interleukin-1 receptor antagonist protein (IRAP) of rabbit annulus fibrosus exposed to IL-1. Maeda suggests that IRAP administration to the disc could be useful in inhibiting the degradation of the disc. Maeda reported that 100 ng rIRAP/ml appears to successfully antagonize 1 ng IL-1β/ml.

In some embodiments, the active agent is cellular. In some embodiments, the cellular agent is a regenerative cell, such as a stem cell or a chondroprogenitor cell. In some embodiments, In some embodiments, the cellular agent is an adipose cell.

Once the enhanced adipose tissue is produced, the treatment may comprise an injection of the enhanced adipose tissue into the intervertebral disc. The enhanced adipose tissue will act both as a bulking agent (due to the presence of substantial native adipose tissue) and as a device for delivering the active agent that has been enhanced.

The adipose tissue may be obtained intra-operatively from any appropriate tissue including the subcutaneous space. The adipose tissue may be harvested by a variety of methods including the use of syringes, vacuum etc. The adipose tissue may be specifically processed to increase its effectiveness for the purpose.

In some embodiments, the adipose tissue may be minced into fine particles to allow ease of injection into the disc. Preferably, the mincing is achieved by mechanical means. Preferably, the mincing produces particles of adipose tissue having an average size of between about 0.1 mm and about 1 mm.

In another embodiment, the mincing is carried out on two separated adipose tissue fraction and with different intensities to produce two specific size fractions of the adipose tissue. The bimodal nature of this combined tissue may advantageously be used to impart specific mechanical functions to the combined tissue. For example, in some embodiments, the first portion is minced to a particle size of about 500 µm and the second is minced to a particle size of about 30 µm. The bimodal nature of this combined tissue provides a higher density upon packing.

In yet another embodiment, at least one portion of the adipose tissue may be activated by a chemical or physical agent to enhance the production of the active agent. In some embodiments, the activation enhances the production of an adipokine, such as adiponectin. In some embodiments, a physical agent such as UV light is shined upon the adipose tissue.

In some embodiment, the activation is performed upon the unseparated native adipose tissue. In some embodiments, the activation is performed upon a separated portion of tissue so that the production of the active agent is enhanced in that portion, the active agent is then concentrated from that separated portion, and then combined with native adipose tissue to produce enhanced adipose tissue In some embodiments wherein native adipose tissue is separated into first and second portions, the volume of the first portion is greater than the volume of the second portion. Accordingly, a relatively greater amount of the active agent can be extracted from the first portion and then combined with the relatively smaller second portion, thereby increasing the concentration effect in the enhanced adipose tissue. In preferred embodiments, the volume of the first portion is 3 times greater than the volume of the second portion. In preferred embodiments, the volume of the first portion is 10 times greater than the volume of the second portion.

When injecting volumes of enhanced adipose tissue into a nucleus pulposus, it is desirable that the volume of the enhanced adipose tissue delivered be no more than 1 cc, preferably no more than 0.5 cc, more preferably between 0.1 cc and 0.3 cc.

In certain cases, instead of using intra-operatively obtained adipose tissue, the invention may rely on the use of other sources of adipose tissue. For instance, culture-expanded adipose cells may be used in accordance with the present invention as a means of obtaining adipose tissue. The source of these cells may be autologous, allogeneic or in certain cases xenogeneic.

In certain cases, the enhanced adipose tissue may be injected along with other cell types or scaffolds. Preferred scaffolds include hyaluronic acid, fibrin gel and small intestine submucosa (SIS).

In some embodiments, growth factors may be added to the enhanced adipose. The growth factors that may be used in accordance with the present invention include, but are not limited to, members of the GDF, and preferably GDF-5 (more preferably rhGDF-5), fibroblast growth factor family, including acidic and basic fibroblast growth factor (FGF-1 and -2) and FGF-4, members of the platelet-derived growth factor (PDGF) family, including PDGF-AB, PDGF-BB and PDGF-AA; EGFs, members of the insulin-like growth factor (IGF) family, including IGF-I and -II; the TGF-β superfamily, including TGF-β1, 2 and 3, osteoid-inducing factor (OIF), angiogenin(s), endothelins, hepatocyte growth factor and keratinocyte growth factor; members of the bone morphogenetic proteins (BMP's) BMP-1, (BMP-3); BMP-2; OP-1; BMP-2A, -2B, and -7; HBGF-1 and -2; members of the hedgehog family of proteins, including indian, sonic and desert hedgehog; ADMP-1; members of the interleukin (IL) family, including IL-1 thru -6; and members of the colony-stimulating factor (CSF) family, including CSF-1, G-CSF, and GM-CSF; cartilage derived morphogenic proteins, such as CDMP-1 and CDMP-2; and isoforms thereof.

In some embodiments, the growth factor is selected from the group consisting of TGF-B, bFGF, and IGF-1. These growth factors are believed to promote regeneration of the nucleus pulposus. Preferably, the growth factor is TGF-B. More preferably, TGF-B is administered in an amount of between 10 ng/ml and 5000 ng/ml, more preferably between 50 ng/ml and 500 ng/ml, more preferably between 100 ng/ml and 300 ng/ml.

In some embodiments, platelet concentrate is provided as the second therapeutic agent. Preferably, the growth factors released by the platelets are present in an amount at least two-fold (more preferably, four-fold) greater than the amount found in the blood from which the platelets were taken. More preferably, the platelet concentrate is autologous. In some embodiments, the platelet concentrate is platelet rich plasma (PRP). PRP is advantageous because it contains growth factors that can restimulate the growth of the ECM, and because its fibrin matrix provides a suitable scaffold for new tissue growth.

In some cases, repair of the annulus may be required prior to or subsequent to the injection of the adipose tissue into the disc.

In some embodiments, the enhanced adipose tissue is liquefied prior to its insertion into the intervertebral disc. The liquification of the adipose tissue will allow it to be injected into the disc through a small bore needle, thereby reducing the level of insult to the annulus fibrosus. However, the temperature of the graft should not be so high as to inactivate the active agent(s).

Because adipose tissue contains more than a single active agent that is desirable, in some embodiments, two active agents are concentrated from at least a first portion of the adipose tissue and then recombined with a second portion of native adipose tissue to produce the enhanced adipose tissue.

Therefore, in accordance with the present invention, there is provided a graft derived from adipose tissue comprising a native level of an active agent, comprising:

a) a first active agent derived from adipose tissue and present at a level greater than the native level of the first active agent in adipose tissue,
b) a second active agent derived from adipose tissue and present at a level greater than the native level of the second active agent in adipose tissue, and
c) (preferably), native adipose tissue.

Also in accordance with the present invention, there is provided a method of making a graft derived from adipose tissue, comprising:

a) obtaining native adipose tissue,
b) separating the adipose tissue into a first portion and a second portion,
c) concentrating a first active agent from the first portion,
d) concentrating a second active agent from the first portion,
e) combining the concentrated agents with the second portion to produce an enhanced adipose tissue, and
f) introducing the enhanced adipose tissue into an intervertebral disc.

Also in accordance with the present invention, there is provided a method of making a graft derived from adipose tissue, comprising:

a) obtaining native adipose tissue,
b) separating the adipose tissue into a first portion, a second portion, and a third portion,
c) concentrating a first active agent from the first portion,
d) concentrating a second active agent from the second portion,
e) combining the concentrated agents with the third portion to produce an enhanced adipose tissue, and
f) introducing the enhanced adipose tissue into an intervertebral disc.

We claim:

1. A graft derived from adipose tissue comprising a native level of an active agent, comprising:
a) native adipose tissue, and
b) a first active agent derived from adipose tissue and present at a level greater than the native level of the active agent in adipose tissue,
wherein the first active agent is adiponectin.

2. The graft of claim 1 wherein the first active agent is present in the graft at a level greater than 10 μg/ml.

3. The graft of claim 1 wherein the native adipose tissue is minced.

4. The graft of claim 3 wherein the minced tissue is characterized by a bimodal size distribution.

5. The graft of claim 1 further comprising:
c) a scaffold.

6. The graft of claim 1 further comprising:
c) a growth factor.

7. The graft of claim 1 further comprising:
c) a second active agent.

* * * * *